United States Patent [19]

Ruch et al.

[11] Patent Number: 4,655,798
[45] Date of Patent: Apr. 7, 1987

[54] PROCESS FOR REMOVING ACETYLENE FROM A $C_2$-STREAM

[75] Inventors: Siegfried Ruch, Dormagen; Karl-Heinz Hagen, Leverkusen; Klaus-Peter Hambrock, Pulheim, all of Fed. Rep. of Germany

[73] Assignee: EC Erdolchemie GmbH, Cologne-Worringen, Fed. Rep. of Germany

[21] Appl. No.: 719,194

[22] Filed: Apr. 3, 1985

[30] Foreign Application Priority Data

Apr. 13, 1984 [DE] Fed. Rep. of Germany ....... 3413898

[51] Int. Cl.$^4$ ............................................. B01D 53/14
[52] U.S. Cl. ............................................. 55/64; 55/48
[58] Field of Search .......................... 55/31, 48, 63–65

[56] References Cited

U.S. PATENT DOCUMENTS

| | | | |
|---|---|---|---|
| 2,146,448 | 2/1939 | Scott et al. | 55/63 X |
| 2,806,552 | 9/1957 | Koble | 55/64 X |
| 2,849,396 | 8/1958 | Nelson | 55/64 |
| 2,907,409 | 10/1959 | Koble | 55/64 |
| 3,004,629 | 10/1961 | Cottle | 55/64 X |
| 3,106,462 | 10/1963 | Cottle | 55/64 X |
| 3,272,885 | 9/1966 | Davison | 55/65 X |
| 3,557,529 | 1/1971 | Ranke | 55/64 X |
| 3,695,002 | 10/1972 | Rottmayr et al. | 55/64 |
| 3,837,144 | 9/1974 | Lewis | 55/64 |

FOREIGN PATENT DOCUMENTS 1944505 2/1972 Fed. Rep. of Germany .
2410713 9/1975 Fed. Rep. of Germany .

Primary Examiner—Robert Spitzer
Attorney, Agent, or Firm—Sprung, Horn, Kramer & Woods

[57] ABSTRACT

Acetylene is removed from a crude $C_2$-stream by scrubbing with an absorbent in an absorption column, a liquid, substantially acetylene-free $C_2$-stream being fed into the absorption column between the feed points for the crude $C_2$-stream and for the absorbent.

15 Claims, 2 Drawing Figures

PROCESS FOR REMOVING ACETYLENE FROM A C$_2$-STREAM

The present invention relates to a process for removing acetylene from crude C$_2$-streams by scrubbing with an absorbent in an absorption column and by further feeding in of a liquid, substantially acetylene-free C$_2$-stream into this absorption column.

In the production of ethylene by thermal cracking of hydrocarbons, such as ethane, propane, liquefied gas, naphtha, gas oil and the like, small amounts of acetylene are also formed. The separation of the gas mixture obtained during such thermal cracking gives fractions of hydrocarbon groups with the same number of carbon atoms, so that the C$_2$-fraction contains acetylene, together with ethane and ethylene, and must be further worked up to obtain pure ethylene.

Ethylene is used on a large industrial scale for ethylation reactions, oligomerization reactions and, in particular, for polymerization. Considerable purity requirements are imposed on the ethylene; for example, the acetylene content of ethylene for polymerization should be not more than 5 ppm.

This purity can be achieved in two ways. One method is selective hydrogenation of the acetylene at various points during working up of the C$_2$-fraction; the second method is absorption of the acetylene with the aid of a selective absorbent, with which it is separated off from the remaining ethylene/ethane mixture. Although selective hydrogenation of the acetylene requires less expenditure on apparatus, it has the disadvantage also that some of the ethylene is thereby lost as ethane, by perhydrogenation. On the other hand, removal of the acetylene by absorption, with a higher expenditure on apparatus, has the advantage that no ethylene is converted into ethane and that the acetylene can be obtained in a pure form as a valuable raw material.

DESCRIPTION OF SPECIFIC EMBODIMENTS

Figure 1:
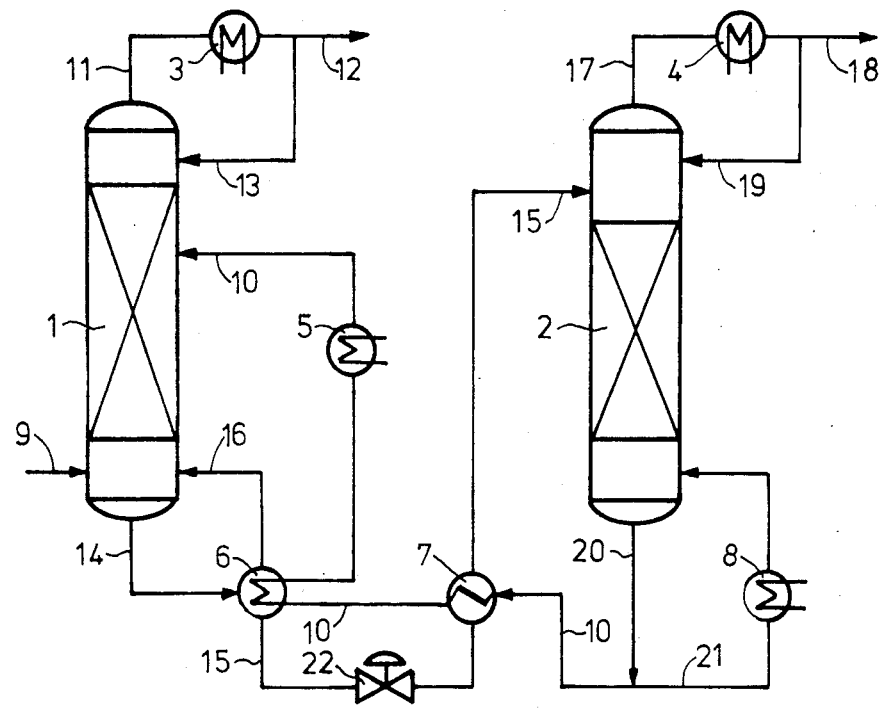
FIG. 1 is a flow diagram showing the absorption of acetylene from a crude C$_2$-stream in accordance with the state of the art.

Removal of acetylene by absorption from a crude C$_2$-stream is known and may be illustrated with the aid of the accompanying FIG. 1:

The absorption process comprises, as the principal apparatus, an absorption column (1), a regeneration column (2) for the absorbent rich in acetylene, condensers (3) and (4) and a cooler (5), and heat exchangers (6) and (7) for heat exchange between the regenerated and the rich absorbent, the rich regenerating agent being let down in an expansion device (21) to a lower pressure than that in the absorption column, and, furthermore, a reboiler (8) for heating the regeneration column (2). For reasons of clarity, pumps and other accompanying apparatus familiar to the expert have been omitted from FIG. 1.

The streams of material in FIG. 1 are the crude, acetylene-containing C$_2$-stream (9), which is fed into the bottom of the absorption column in gaseous form and is freed from the acetylene in countercurrent by the absorbent (10) flowing down; part of the top product (11) of the absorption column (1) is passed to further working-up as acetylene-free ethylene/ethane mixture (12), and part is reintroduced, after condensation, as a reflux (13) onto the absorption column (1); the absorbent (14) which is rich in acetylene and is obtained in the bottom of the absorption column (1) is initially warmed in the heat exchanger (6) by regenerated absorbent, some of the dissolved gases, preferably ethane and ethylene, being expelled and recycled as a gaseous stream (16) to the lower part of the absorption column (1); the absorbent (15), which is now enriched with acetylene, passes to the regeneration column (2), after being let down in the expansion apparatus (22) and renewed heat exchange in the heat exchanger (7); the acetylene-rich top product (17) of the regeneration column (2) is cooled in (4), stream (18) is removed for working up to acetylene and the absorbent (19) which has condensed out is recycled to the regeneration column (2); part of the regenerated absorbent (20) obtained in the bottom of (2) is recycled as stream (21) via the reboiler (8) to (2), and part is recycled as stream (10) via the heat exchangers (7) and (6) to (1), the required temperature being established in (5).

The absorption process described has reached a high state of development. Nevertheless, the necessity of the C$_2$-reflux (13) is a considerable disadvantage of this process. On the one hand, this reflux causes an additional load on the absorption column with C$_2$-substances. Furthermore, unstable operating conditions arise at the transition point between the reflux section and the feed point of the absorbent in the absorption column, and these lead to flooding when the absorption column is subjected to higher loads. In order to ensure reliable operation, it is therefore necessary to maintain an adequate distance from this flooding point, which in an existing installation leads to restrictions in capacity and in a new installation leads to the need for larger apparatuses. Moreover, the condensate used for the reflux (13) is in temperature/pressure equilibrium, which means that only slight variations in pressure or temperature lead to flashing of the liquid on the suction side of the feed pump for the reflux; such flashing leads to cavitation of the pump. Such cavitation not only leads to an accelerated wear of the pump but also causes the reflux onto the absorption column to stop. As a result of the stop in the reflux, the temperature of the absorption column increases suddenly, so that acetylene breaks through to the top product. In such cases, all the ethylene production contaminated by acetylene must then be burned as useless because the acetylene specification limit has been exceeded.

Attempts have already been made to control the irregularities described, for example by presaturation of the absorbent with ethylene, by changing the temperature program of the absorption column or by adding anti-foaming agents. However, all of the solution attempts mentioned were unsuccessful.

Surprisingly, it has been found that by feeding in a liquid, substantially acetylene-free C$_2$-stream into the absorption column, the amount of the reflux at the top of the absorption column can be considerably reduced and can even be rendered completely superfluous, so that the disadvantages mentioned are reduced or can be completely eliminated.

The invention thus relates to a process for removing acetylene from a crude $C_2$-stream by scrubbing with an absorbent in an absorption column, which is characterised in that a liquid, substantially acetylene-free $C_2$-stream is fed into the absorption column between the feed points for the crude $C_2$-stream and for the absorbent.

Liquid ethane, liquid ethylene or a liquid ethane/ethylene mixture is suitable as the liquid, substantially acetylene-free $C_2$-stream. The substances mentioned can contain up to 2% of acetylene, preferably up to 1% of acetylene and particularly preferably up to 0.1% of acetylene. Such $C_2$-streams are available at many points in a plant for the production of ethylene, for example the bottom product of the methane column, the condensate from heating of the ethylene column, the condensate of the top product of the absorption column and the pure ethylene or ethane substantially freed from ethylene obtainable in the production of ethylene. An ethane/ethylene condensate, for example that of the absorption column, or pure ethylene is used as the $C_2$-stream according to the invention because it is particularly readily available. The use of pure ethylene is particularly preferred here, because no foreign substances which are to be regarded as ballast substances in the context of ethylene production are fed in with the pure ethylene.

Such liquid $C_2$-streams to be used according to the invention have a temperature of $-100°$ C. to $-30°$ C. and are under a pressure which corresponds at least to the pressure required for liquefaction of such a $C_2$-stream at the temperature mentioned. A $C_2$-stream corresponding to the temperature and pressure conditions of the absorption column is preferably used. The absorption column is operated under a pressure range of from 4 to 20 bar, preferably 5 to 15 bar, at the associated saturation vapour temperature of the crude $C_2$-stream to be purified; this temperature range varies from about $-74°$ C. to about $-30°$C. Under the circumstances mentioned, it is again preferable to remove the liquid $C_2$-stream to be fed in according to the invention from a higher pressure level than that prevailing in the absorption column; by this measure, a feed pump can be dispensed with, which means that any cavitation phenomena on its suction side and the disturbances discussed above are avoided.

The liquid $C_2$-stream to be fed in according to the invention is fed into the absorption column in an amount of 1-4%, preferably 1.3-3.3%, particularly preferably 1.5-2.5%, based on the amount of the crude $C_2$-stream. In the case where the absorption column and hence also the $C_2$-stream to be fed in are at a lower temperature in the stated range of saturation vapour temperatures, the amount of liquid $C_2$-stream to be fed in can be in the lower part of the stated range, and vice versa.

The liquid, substantially acetylene-free $C_2$-stream is fed, according to the invention, into the absorption column between the feed points for the crude $C_2$-stream and for the absorbent. An absorption column with a total of 5-30 trays, preferably 5-20 trays, is used here. The crude $C_2$-stream is fed in here below the first tray or on the 1st-5th tray, preferably below the 1st tray. The recycle gas (16) expelled from the bottom discharge (14) in the heat exchanger (6) is also fed in, independently of the crude $C_2$-stream, below the 1st tray or at the 1st-5th tray, preferably below the 1st tray.

The absorbent is fed in at the 3rd-6th tray from the top end of the column.

The liquid, substantially acetylene-free $C_2$-stream according to the invention is now fed in at a point from the 2nd tray of the absorption column to below the feed point of the absorbent, the crude $C_2$-stream still being fed in below the liquid $C_2$-stream according to the invention, in agreement with the above statements. The liquid $C_2$-stream according to the invention is preferably fed in at least three trays below the feed point for the absorbent.

In the process according to the invention, the absorption column can be operated with a reflux at the top, as in conventional processes. However, this reflux is preferably reduced in comparison with the amounts previously regarded as necessary. A suitable amount by which the reflux is reduced is at least the amount corresponding to the liquid, substantially acetylene-free $C_2$-stream to be fed in according to the invention. If, for example, a reflux onto the absorption column of 10-15% of the total $C_2$-throughput was regarded as necessary to achieve an ethylene which meets the specification in respect of the acetylene content, and the rate of liquid, substantially acetylene-free $C_2$-stream fed in is set at the abovementioned rates of 1-4% of the total $C_2$-throughput, the reflux at the top of the absorption column can be reduced to values of 6-14% of the total $C_2$-throughput in the context of the process according to the invention. In an other preferred process variant, however, the reflux is reduced by a larger amount than that corresponding to the liquid $C_2$-stream fed in according to the invention, for example by 1-10 times the amount of the liquid $C_2$-stream fed in according to the invention, the upper limit of this range (reduction by a factor of 10) representing the case, for example, where a reflux at the level of 10% (15%) of the total $C_2$-feed was regarded as required in the conventional process variant and the amount of liquid $C_2$-stream fed in according to the invention was set at a level of 1% (1.5%) of the total $C_2$-throughput. In this extreme case, the reflux hitherto regarded as necessary is thus completely dispensed with. It has now been found, surprisingly, that excellent results are obtained with this variant, that is to say with the reflux hitherto regarded as necessary completely dispensed with, so that completely dispensing with the reflux represents a particularly preferred variant of the process according to the invention.

Possible absorbents are all those which have a selective dissolving power for acetylene in preference to ethylene and ethane, for example N-alkyl-pyrrolidones, for example N-methyl-2-pyrrolidone, dialkylformamides, for example dimethylformamide or diethylformamide, and lower aliphatic ketones, for example acetone or methyl ethyl ketone. In the case where these selectively dissolving absorbents have a melting point above the desired operating temperature of the absorption column, the absorbent can be used as a mixture with low-boiling lower aliphatic alcohols, for example as a mixture with methanol, ethanol, n-propanol, i-propanol, n-butanol or sec.-butanol. The content of the above low-boiling alcohol in the mixture with the selectively dissolving absorbent can be 5-30% by weight, as is known.

The process according to the invention has the following advantages, which were not hitherto regarded as being possible:

1. The reflux onto the absorption column can be reduced or completely dispensed with.

2. In connection with 1., the energy consumption for removing acetylene can be reduced, especially in the preferred process variants, since the amount of liquid $C_2$-stream fed in according to the invention is considerably smaller than the reflux hitherto regarded as necessary.

3. By reducing or completely dispensing with the reflux, the flooding otherwise observed in the column under higher loads is reduced or eliminated completely; a more reliable operating procedure is thereby ensured.

4. In connection with 3., the capacity of the absorption column can be increased, for the same separation efficiency, by at least 6%, in many cases by about 16%, of the original nominal capacity.

5. In new installations, the upper reflux trays, the condenser for the top product and the reflux drum, including the associated pumps, can be dispensed with, which means that investment costs are reduced.

6. If the $C_2$-feed liquid according to the invention is removed from a process stage with a higher pressure level than that in the absorption column, pump delivery can be dispensed with, which means that the known disadvantages, for example cavitation on the suction side of the pump, are eliminated. The reliability of continuous operation is also thereby noticeably increased; product degradation, for example by conversion of ethylene which does not meet the specification in the troublesome case where only the calorific value can be credited, is avoided.

7. The acetylene-free topstream of the absorption column is obtained with a higher temperature when the reflux is reduced or completely dispensed with, and provides an additional energy advantage for the subsequent ethylene-ethane separation; it can thus be expected that the topstream is obtained with a temperature of about $-30°$ C. in the process according to the invention, instead of about $-48°$ C. as hitherto, and no longer has to be condensed, since the ethylene/ethane mixture is in general fed into the ethylene/ethane separation in gaseous form.

Figure 2:
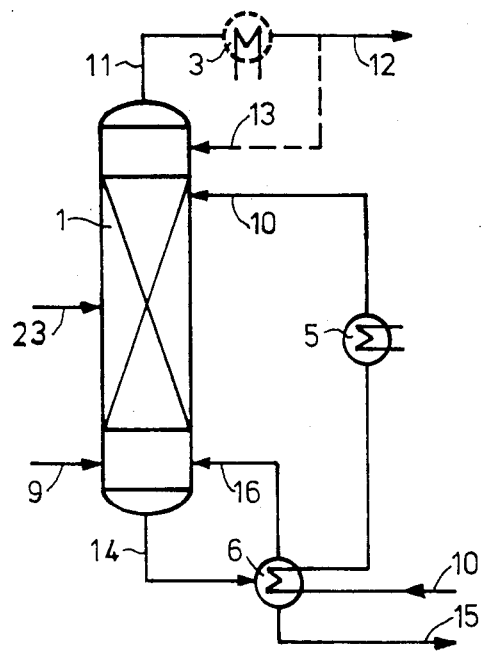
FIG. 2 is a similar flow diagram to that of FIG. 1 showing the removal of acetylene by absorption from a crude C$_2$-stream according to the invention in which there is introduced into the absorption column at a point intramediate the feed point of the crude C$_2$-stream and the feed point of the absorbent a liquid substantially acetylene-free C$_2$-stream.

The general embodiment of the process according to the invention is shown with the aid of FIG. 2. FIG. 2 contains only the absorption column (1) to which the regeneration column (2) as has been shown in FIG. 1 is connected in unmodified form. Where the apparatuses and substance streams match those shown in FIG. 1, they have been given the same numbers. As an addition to FIG. 1, the liquid, substantially acetylene-free $C_2$-flow to be fed in according to the invention is shown as (23) in FIG. 2. The reflux (13) onto (1) and the heat exchanger (3) is shown with a broken line in FIG. 2, since it can be reduced or completely dispensed with, as desired, in accordance with the preceding description.

EXAMPLES

Example 1 (for comparison)

Acetylene is removed with an N-methyl-pyrrolidone (NMP)/methanol mixture in a weight ratio of 85/15 in an existing thermal cracking plant for the production of ethylene, with a design capacity of 366,400 tonnes per year of ethylene. The absorption column contains 24 bubble trays and is divided into 2 column sections. Above the bottom 19 trays, the absorbent flows from the top downwards in counter-current to the ascending crude $C_2$-stream, whilst an acetylene-free $C_2$ top condensate is passed as a reflux over the top 5 trays. When the design value of 55 tonnes/hour for the feed of crude $C_2$-stream was exceeded by more than 2%, the absorption column immediately flooded and production difficulties and loss of product therefore occurred, because ethylene which did not meet the specification could be used only as fuel gas. The reflux here was 6.6 tonnes/hour.

Example 2 (according to the invention)

In the same absorption column as in Example 1, the absorbent NMP/methanol was introduced at the 19th tray, as previously. A liquid stream of pure ethylene at a rate of 1.2 tonnes/hour was introduced at the 12th tray. The reflux could be completely dispensed with. The feed of crude $C_2$-stream could be increased to 64 tonnes/hour, without the column flooding. The increase in throughput corresponds to an ethylene production of 426,400 tonnes per year.

What is claimed is:

1. In a process for removing acetylene from a crude $C_2$-stream by introducing the same into an absorption column and therein introducing an absorbent at a point above the point at which said crude $C_2$-stream is introduced and therein absorbing acetylene in said absorbent, the improvement wherein a stream consisting of liquid $C_2$ which is substantially acetylene free is fed into the absorption column between the feed points of the crude $C_2$-stream and for the absorbent.

2. A process according to claim 1 wherein the liquid substantially acetylene free $C_2$-stream is an ethylene, ethane or ethylene/ethane stream.

3. A process according to claim 1 wherein said liquid substantially acetylene free $C_2$-stream is substantially pure ethylene.

4. A process according to claim 1 wherein said liquid substantially acetylene free $C_2$-stream is introduced into said absorption in an amount of 1 to 4 percent by weight upon the weight of said crude $C_2$-stream.

5. A process according to claim 1 wherein said liquid substantially acetylene free $C_2$-stream is introduced into said absorption column in an amount of 1.3-3.3 percent by weight based upon the weight of said crude $C_2$-stream.

6. A process according to claim 1 wherein said liquid substantially acetylene-free $C_2$-stream is introduced into said absorption column in an amount of 1.5-2.5 percent by weight based upon the weight of said crude $C_2$-stream.

7. A process according to claim 1 wherein at the top of said absorption column there is withdrawn a $C_2$-stream and a portion of said $C_2$-stream is refluxed back to the absorption column but the rate of reflux is reduced by at least the amount of $C_2$-stream fed into said absorption column between the feed points for the crude $C_2$-stream and for the absorbent.

8. A process according to claim 1 wherein the process is carried out without refluxing $C_2$-stream removed from the top of the absorption column.

9. A process according to claim 1 wherein said liquid substantially acetylene-free $C_2$-stream is one in which, in the subsequent working up process of the top product of the absorption column, is under a higher pressure than the pressure in the absorption column.

10. A process according to claim 1 wherein the absorbent is an N-alkyl-pyrrolidone.

11. A process according to claim 1 wherein said absorbent is N-methyl-2-pyrrolidone.

12. A process according to claim 1 wherein said absorbent is a dialkylformamide.

13. A process according to claim 1 wherein said absorbent is dimethylformamide or diethylformamide.

14. A process according to claim 1 wherein said absorbent is a lower aliphatic ketone.

15. A process according to claim 1 wherein said absorbent is acetone or methylethyl ketone.

* * * * *